United States Patent [19]
Fukuyama et al.

[11] Patent Number: 5,928,633
[45] Date of Patent: Jul. 27, 1999

[54] MATERIAL FOR ELIMINATION OR DETOXIFICATION OF SUPER ANTIGENS

[75] Inventors: Mayumi Fukuyama, Shiga; Keishi Miwa, Osaka; Kazuo Ishikawa, Shiga, all of Japan

[73] Assignee: Toray Industries, Inc., Japan

[21] Appl. No.: 08/645,452

[22] Filed: May 13, 1996

[30] Foreign Application Priority Data

May 16, 1995 [JP] Japan ................................. 7-117175
Dec. 28, 1995 [JP] Japan ................................. 7-344204

[51] Int. Cl.⁶ .................................................. A61K 31/73
[52] U.S. Cl. ................................... 424/78.31; 424/78.32; 424/78.33; 424/78.35; 424/78.36; 424/78.37; 424/78.38; 424/88; 424/520; 424/406; 514/55; 514/585; 514/596
[58] Field of Search .......................... 514/55, 585, 596, 514/597; 424/520, 529–531, 88, 78.31, 78.32, 78.33, 78.35–78.38, 406

[56] References Cited

U.S. PATENT DOCUMENTS

| | | | |
|---|---|---|---|
| 3,230,141 | 1/1966 | Frick et al. | 514/597 |
| 4,267,313 | 5/1981 | Sannan et al. | 536/18 |
| 4,474,806 | 10/1984 | Beattie et al. | 514/596 |
| 4,661,260 | 4/1987 | Kodama et al. | 210/679 |
| 4,680,367 | 7/1987 | Kopp et al. | 528/44 |
| 5,482,947 | 1/1996 | Talley et al. | 514/311 |
| 5,612,377 | 3/1997 | Crooks et al. | 514/596 |
| 5,614,550 | 3/1997 | Yoshida et al. | 514/450 |

FOREIGN PATENT DOCUMENTS

| | | |
|---|---|---|
| 0 355 047 | 2/1990 | European Pat. Off. . |
| 1 644 815 | 2/1971 | Germany . |
| 3438527A1 | 4/1986 | Germany . |
| 46-1437 | 1/1971 | Japan . |
| 63-186660 | 2/1988 | Japan . |
| 4-114661 | 4/1992 | Japan . |
| 7-48431 | 2/1995 | Japan . |
| 1 249 194 | 10/1971 | United Kingdom . |

OTHER PUBLICATIONS

Fleischer APMIS 102 3–12, 1994 Superantigens.
CHITOPEARL (Technical Information of Fuji Spinning Co., Ltd.) written in Japanese and English 1994.
Patent Abstracts of Japan vol. 012, No. 181 (C–499), May 1988 & JP 62 288602 A (Agency of Ind Science & Technol), Dec. 1987.
Database WPI Section Ch, Week 8836 Derwent Class A96, AN 88–254713 XP002062558 & JP 63 186 660 A (UBE Ind. Ltd.) Aug. 1988 Abstract.
Muzzarelli et al "Chitin–based poly(urea–urethane)s" J. Biomater. Sci. Polym. Ed., vol. 6, No. 6, 1994, pp. 541–547, XP002062553 p. 546, paragraph 2.
Moore et al "Reactions of chitosan: 4. Preparation of organosoluble derivatives of chitosan" Int. J. Biol. Macromol., vol. 4, No. 4, 1982, pp. 246–249, XP002062554 p. 247, paragraph 4, p. 249, paragraph 3.
Aiba et al "Covalent immobilization of chitosan derivatives onto polymeric film surfaces . . . " Biomaterials, vol. 8, No. 6, 1987 pp. 481–488, XP002062555 abstract; fig. 2.
Butcher et al "Immunologic Studies of Hollow–Fiber Dialyzer Extracts" Artificial Organs, vol. 8, No. 3, 1984, pp. 318–328, XP002062556 Abstract p. 318, col. 1, paragraph 1, col. 2, paragraph 1.
Fan'Kovskaya et al "Production and Certain Properties of Staphylococcal Toxin, Inducing Toxic Shock Syndrome" Mol. Genet. Mikrobiol. Virusol., vol. 7, 1987, pp. 23–27, XP0020062557.
Data base WPI Section Ch, Week 8823 Derwent Class A11, AN 88–157861 XP002062559 & JP63 097 633 A (Fuji Spinning Col Ltd.) Apr. 1988 Abstract.

*Primary Examiner*—Neil S. Levy
*Attorney, Agent, or Firm*—Nixon & Vanderhye

[57] ABSTRACT

A material with excellent selective absorption of super antigens. Said material contains urea bonds or thiourea bonds and remains active even in a high protein concentration solution in the neutral region, Activity remains after sterilization. Also provided is a body fluid purifying column for eliminating or detoxification of super antigens. In addition to that, this invention provides a wound dressing material with super antigen adsorbing properties.

25 Claims, 3 Drawing Sheets

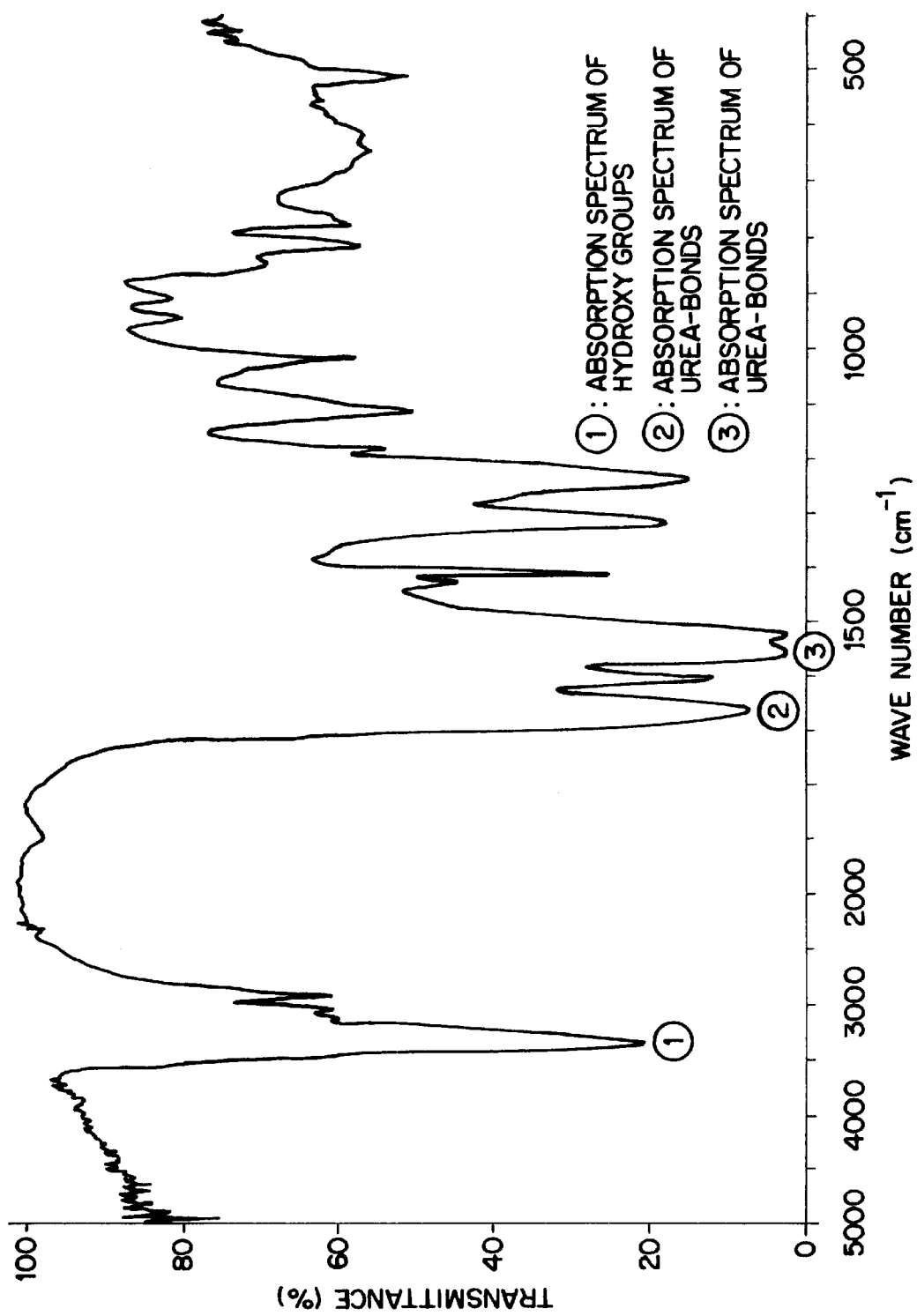

MATERIAL FOR ELIMINATION OR DETOXIFICATION OF SUPER ANTIGENS

FIELD OF THE INVENTION

The present invention relates to a material for detoxification or elimination of super antigens such as staphylococcal enterotoxin and streptococcal exotoxin. This material binds with super antigens existing in a protein solution at a high concentration such as in the human blood etc., it is preferably used as an antidote for reducing or eliminating toxic activity of super antigens, in a purification column for eliminating super antigens or a wound dressing material.

DESCRIPTION OF THE RELEVANT ART

Super antigens are a group of proteins which can directly bind with major histocompatibility antigen class II proteins (hereinbelow it is called "MHC class II" in some cases) on an antigen presenting cell without passing through processing in the antigen presenting cell super antigens are different from conventional antigens and furthermore, stimulate a T-cell by forming a complex of this MHC class II and the T cell. Several restrictions exist in binding the T-cell for the conventional antigens, and number of T-cells reacting with conventional antigens is usually at most one per ten thousand, but as the super antigen binds only to the variable region of the β-chain of the T-cell receptor, certain kinds of super antigens stimulate one T-cell among five T-cells. As the result, it is thought that super antigens stimulate extraordinarily the immune system to generate fevers, rash and hypotension during sepsis and vomiting during food poisoning or autoimmune diseases (D. L. Murray et al, American Society of Microbiology News. 61 (5) p229 (1995)). As the super antigens, staphylococcal enterotoxin, Streptococcal exotoxin, Yersinial exotoxin, certain virus proteins and heat shock proteins have been confirmed and it is possible that other super antigens will be found in the future.

Up to this time, as those substances which have affinity with these super antigens, antibodies to these super antigens have been described (P. M. Rosten et al. Journal of Clinical Microbiology 25(2) p327 (1987)), major histocompatibility antigen class II proteins and thereof (J. K. Russell et al. Biochemical and Biophysical Research Communications, 168, p696 (1990)), ion exchange resins (H.Igarashi etc., Infection and Immunity 44(1) p175 (1984)) etc., are known and they have been used as binding substances for adsorbing super antigens in blood and culture supernatant. However, most of these binding subtances are proteins and peptides and they are easily deactivated by sterilization. In addition, affinity between ion exchange resins and super antigens is easily reduced by the influence of pH of the solution; specificity is decreased in the neutral region. Therefore, they are not suitable as a material having sufficient affinity for super antigens in solutions having a high protein concentration as blood, foods etc., where the pH should be kept neutral.

OBJECT OF THE INVENTION

The present invention has as its objective, to solve the disadvantages of the conventional technologies by providing a material with excellent selective affinity for super antigens even in a highly concentrated protein solution at a pH in the neutral region, possessing residual activity after sterilization and are also inexpensive. Namely, the material of the present invention has a high affinity for super antigens and it can bind with super antigens existing in body fluids such as blood and urine, foods, drinks and medicines. It is possible by these bindings that the toxin-like activities of the super antigens can be eliminated (detoxification) by changing such properties of the super antigens as their conformations or by shielding the binding sites with MHC class II or/and T-cells. Namely, when the material of the present invention is used as a medicine, it is possible to effectively treat the effects of food poisoning, sepsis and autoimmune diseases or to prevent them from occurring. In addition, if this material is water-insoluble, it becomes possible to eliminate super antigens from body fluids such as blood and urine, foods, drinks and medicines to to treat the effects of food poisoning, sepsis and autoimmune diseases and to prevent them from occurring. Especially, it is suitable as a body fluid purifying column for eliminating super antigens or as a super antigen-adsorbing wound dressing material. In addition, it may be used as a quantitative measuring material making it possible to diagnose food poisoning, sepsis and autoimmune diseases. The present invention provides a material which enables diagnosis and therapy of these diseases and to prevent them from occurring.

SUMMARY OF THE INVENTION

We found that a material containing a urea bond or a thiourea bond has an affinity with staphylococcal enterotoxin and Streptococcal exotoxin. That is, the first aspect of the present invention is a material for eliminating or detoxifying super antigens wherein said material comprises a urea bond or a thiourea bond. The material preferably comprises a group capable of forming a hydrogen bond and an aromatic substituent.

A second aspect of the present invention is a urea or thiourea compound of the following formula:

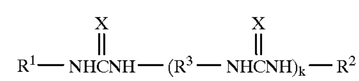

which compound contains a group capable of forming a hydrogen bond and an aromatic substituent, and X is O or S;

k is 0 or a positive integer;

each of $R^1$, $R^2$, $R^3$, may be the same or different, is any one of a group capable of forming a hydrogen bond or an aromatic substituent.

Where K≧2, it is preferable that a unit having a group capble of forming a hydrogen bond and a unit having an aromatic substituent are alternatively appeared.

As a group capable of forming a hydrogen bond, an amino group or a hydroxyl group; particularly, a secondary amino group or a tertiary amino group is prefarable.

The third aspect of the present invention is a body fluid purifying column comprising the above mentioned material.

The fourth aspect of the present invention is a wound dressing material comprising the above mentioned material.

DETAILED DESCRIPTION OF THE INVENTION

There are no special limitations as the substituent of the urea bond or the thiourea bond and aliphatic compounds such as a hexyl group, octyl group and dodecyl group and alicyclic compounds such as cyclohexane and cyclopentane are used, but aromatic compounds such as a phenyl group, naphthyl group and anthranyl group are more preferably used. In addition, derivatives such derivatives as aminohexyl group, monomethylaminohexyl group, dimethylaminohexyl group, aminooctyl group, aminododecyl group and tolyl group, chlorophenyl group, nitrophenyl group, diphenylmethyl group and aminodiphenylmethyl group are also preferably used. In addition, compounds containing a group capable of forming hydrogen bonds such as amino group, hydroxyl group, carboxyl group and mercapto group are preferably used as substituents. For example, such compounds as having hydroxyl group, hydroxypropane, 1,3-diamino-2-hydroxypropane, hydroxybutanone, hydroxybutyric acid and hydroxypyrimidine and glucides such as monosaccharides, oligosaccharides and polysaccharides such as glucose, glucosamine, galactosamine, maltose, cellobiose, sucrose, agarose, cellulose, chitin, chitosan and derivatives thereof, and such compounds as having amino group, diethylenetriamine, triethylenetetramine, tetraethylepentamine, dipropylenetriamine, polyethyleneimine, N-methyl-2,2'-diaminodiethylamine are preferably used. The material of the present invention can have most preferably both an aromatic compound and a group capable of forming a hydrogen bond such as an amino group or a hydroxyl group-containing compound (including glucides or their derivatives) as substituents of a urea bond or a thiourea bond.

In addition, as either monomers, oligomers or polymers can be used as the material of the present invention, such compounds as polymerized compounds of the above described substituents or a part thereof are also in the range of materials of the present invention. Namely, as the above described substituents or a part thereof, a repeating unit of synthetic polymers such as nylon, polymethyl methacrylate, polysulfone, polystyrene, polyethylene, polyvinyl alcohol and polytetrafluoroethylene and natural polymers such as cellulose, collagen, chitin, chitosan and their derivatives, are preferably used. Namely, it is preferably performed to introduce urea bonds or thiourea bonds into these synthetic polymers prepared of homopolymerization, copolymerization, blending and natural polymers. In addition, those products prepared by coating an inorganic material such as metals, ceramics and glass with an appropriate polymer are also preferably used.

In addition, polyurea or polythiourea wherein a plurality of urea bonds or thiourea bonds exist in the molecular structure is preferable as a material of the present invention. In this case, any one of the above described substituents can be used as the substituent of the urea bond or the thiourea bond, it is most preferable to incorporate both an aromatic compound and a compound having a group capable of forming a hydrogen bond such as amino group or hydroxyl group-containing compound (including glucides and their derivatives).

The material of the present invention can be synthesized by generally known methods. For example, when a urea bond or a thioures bond is introduced into an aliphatic compound and an aromatic compound, a method wherein an isocyanate derivative or an isothiocyanate derivative is reacted with an amino compound can be used. As the isocyanates or the isothiocyanates, for example, aliphatic isocyanates or isothiocyanates such as ethyl isocyanate, stearyl isocyanate, n-butyl isocyanate, iso-butyl isocyanate, n-propyl isocyanate, methyl isothiocyanate, ethyl isothiocyanate, n-butyl isothiocyanate, benzyl isothiocyanate, hexamethylenediisocyanate, cyclohexyl isocyanate, cyclohexylisothiocyanate and cyclohexyldiisocyanate can be used, but aromatic isocyanates or isothiocyanates such as phenyl isocyanate, chlorophenyl isocyanate, fluorophenyl isocyanate, bromophenyl isocyanate, nitrophenyl isocyanate, tolylphenyl isocyanate, methoxyphenyl isocyanate, 1-naphthyl isocyanate, 4,4'-diphenylmethanediisocyanate, 3,3',5.5'-tetraethyl-4,4'-diisocyanatediphenylmethane, phenyl isothiocyanate, chlorophenyl isothiocyanate, fluorophenyl isothiocyanate, nitrophenyl isothiocyanate, tolyl isothiocyanate, methoxyphenyl isothiocyanate and 1-naphthyl isothiocyanate, are more preferably used. In addition, as amino group of the amino compounds used in the present invention, either of primary amino group, secondary amino group or tertiary amino group can be used and as amino compound, for example, either one of sec-octyl-amine, 6-amino-n-caproic acid, 3-amino-1-propene, $\alpha$-amino-isobutyric acid, aminopyridine, aminobenzenesulfonic acid, diethylenetriamine, triethylenetetramine, tetraethylenepentamine, dipropylenetriamine, N-methyldiaminodiethylamine, polyethyleneimine etc., can be used, however taking the reactivity of the amono group into consideration, it is preferable to have primary amino group at least one at the reaction site. In addition, amino compounds with a hydroxyl group can be more preferably used. Namely, aliphatic amines such as 2-ethanolamine, 3-propanolamine, 6-hexanolamine, 1,3-diamino-2-hydroxypropane and glucamine and derivatives of N-methyl-1,3-diaminopropanol or aromatic amines such as 4-aminophenol, diaminophenol, aminohydroxypyrimidine, diaminohydroxypyrimidine and diamonohydroxypyrazole or amino acids such as serine and tyrosine can be used. In addition, it is preferred that an amino compound with a hydroxyl group is synthesized from a compound only with a hydroxyl group or a compound only with an amino group by reacting it with epichlorohydrin and an amino compound or 1,3-dibromo-2-hydroxypropane etc. In this case, the mixing ratio of the amino compound to an isocyanate derivative or an isothiocyanate derivative can be arbitrarily selected and it is preferable that the amount of amino group is an equimolecular quantity or excess to the amount of isocyanate group to suppress the reaction of the hydroxyl group with isocyanate or isothiocyanate group. In addition, when urea bonds or thiourea bonds are introduced into a glucide, the same method as described above can be used. Namely, when a glucide with an amino group such as chitosan or glucosamine is used, the above described isocyanate derivative or isothiocyanate derivative can be reacted. In the case of such a glucide that has no amino group as cellulose, after the hydroxyl group of the glucide is activated using epichlorohydrin or trisilchloride, an amino group is introduced by reacting it with ammonia or diaminoethane and urea bonds or thiourea bonds can be introduced into a glucide utilizing this amino group.

In addition, when the material of the present invention is an oligomer or a polymer, for example, a method wherein an oligomer or a polymer with an isocyanate group, a carboxyl group or an active ester group of a carboxylic acid such as succinimide group is reacted with the amino group of a urea derivative or a thiourea derivative, is preferably used. As the amino group used in the reaction, because of low reactivity of the terminal amino group of the urea bond or the thiourea bond, it is preferable to use an amino group existing on another position. In addition, a method wherein an oligomer and a polymer each with an amino group or an oligomer and a polymer wherein an amino group is introduced by using ammonia, diamonoethane, 1,3-diaminopropane, 1,3-diamino-2-hydroxypropane are reacted with an isocyanate derivative or an isothiocyanate derivative, is a preferable. Functional groups such as amino groups, isocyanate groups, carboxyl groups, an active ester group of a carboxylic acid such as a succinimide group can be introduced if necessary, into an oligomer and a polymer.

In addition, when the material of the present invention is polyurea or polythiourea, for example, a method wherein a polyisocyanate derivative or a polyisothiocyanate derivative is reacted with a polyamino compound can be used. Ordinarily, as the amount of the reagent, 0.1–5 mole polyamine is preferably used to 1 mole polyisocyanate or polyisothiocyanate. As the polyisocyanate or polyisothiocyanate, hexamethylenediisocyanate, cyclohexyldiisocyanate, tolylene diisocyanate, 4,4'-diphenylmethanediisocyanate, 3,3',5,5' tetraethyl-4,4'-diisocyanatediphenylmethane, xylylene diisocyanate, methylene-bis(4-phenyl isothiocyanate) etc., are preferably used. In addition, as the polyamino compound, diaminoethane, diaminopropane, 1,3-diaminio-2-hydroxypropane, N-methyl-1,3-diamino-2-propanol, diamino-phenol, N,N'-diaminopiperazine, diethylenetriamine, triethylenetetramine, tetraethylenpentamine, polyethyleneimine, dipropylenetriamine, N-methyldiaminoethylamine etc., are preferably used.

All the above described reactions are performed as the standard at a reaction temperature of 0–150° C. and for a reaction time of 0.1–24 hours. In addition, even though the reaction solvent is not always necessary, but the reaction is ordinarily performed in the presence of a solvent. As the solvents which can be used, aliphatic hydrocarbons such as methanol, ethanol, isopropyl alcohol, n-butanol, hexane, acetone, N,N-dimethylformamide and dimethyl sulfoxide, aromatic hydrocarbons such as benzene, toluene and xylene, halogenated hydrocarbons such as dichloromethane, chloroform and chlorobenzene, ethers such as diethyl ether, tetrahydrofuran and dioxane are cited. The product can be purified by column chromatography and recrystallization after the reaction liquid is treated by such an ordinary aftertreatment as filtration and concentration. In addition, in the case of a water-insoluble material, washing it by using a glass filter is also a preferable method.

Water-insoluble materials of the present invention are preferably used for a super antigen elimination column, a wound dressing material, a quantitative measuring material etc. There is no special limitation on their shapes and when they are used as an elimination column, such shapes as beads, fibers, hollow fibers, yarns, nets, braids, woven or knitted fabrics of coarse structure (randomly packed, spirally wound or packed with fragments thereof) etc., are preferable and in the case of wound dressing materials, such shapes as fabrics, films etc., are preferable. As materials having urea bonds, porous chitosan beads, "CHITOPEARL BCW-3001" and "CHITOPEARL BCW-3501" (Fuji Spinning Co., Ltd) are commercialized. However, these chitosan beads have been used as carriers for enzyme immobilization and are not yet known to have an affinity for super antigens. On the other hand, polyether urethane urea has urea bond and has been used as a material for medical use, however, it does not have affinity for super antigens.

BRIEF DESCRIPTION OF THE DRAWINGS

FIG. 3 shows an infrared spectrum of a polyurea derivative.

DESCRIPTION OF THE PREFERRED EMBODIMENTS

The present invention will be explained in detail hereinbelow by using examples but the contents of the invention are not restricted by the examples.

EXAMPLE 1

Introduction of urea bonds into chitosan beads and a super antigen adsorption test using said beads 12 ml (it was sedimentary volume and the dry weight was 1.0 g) chitosan beads ("CHITOPEARL AL-01" manufactured by Fuji Spinning Co., Ltd.) with a structural formula (1) and a particle diameter of 0.1 mm were stirred in 20 ml N,N-dimethyl-formamide for five minutes. Then the beads and the solution were separated by means of a glass filter.

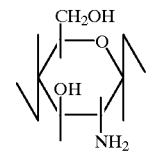
(1)

Figure 1:
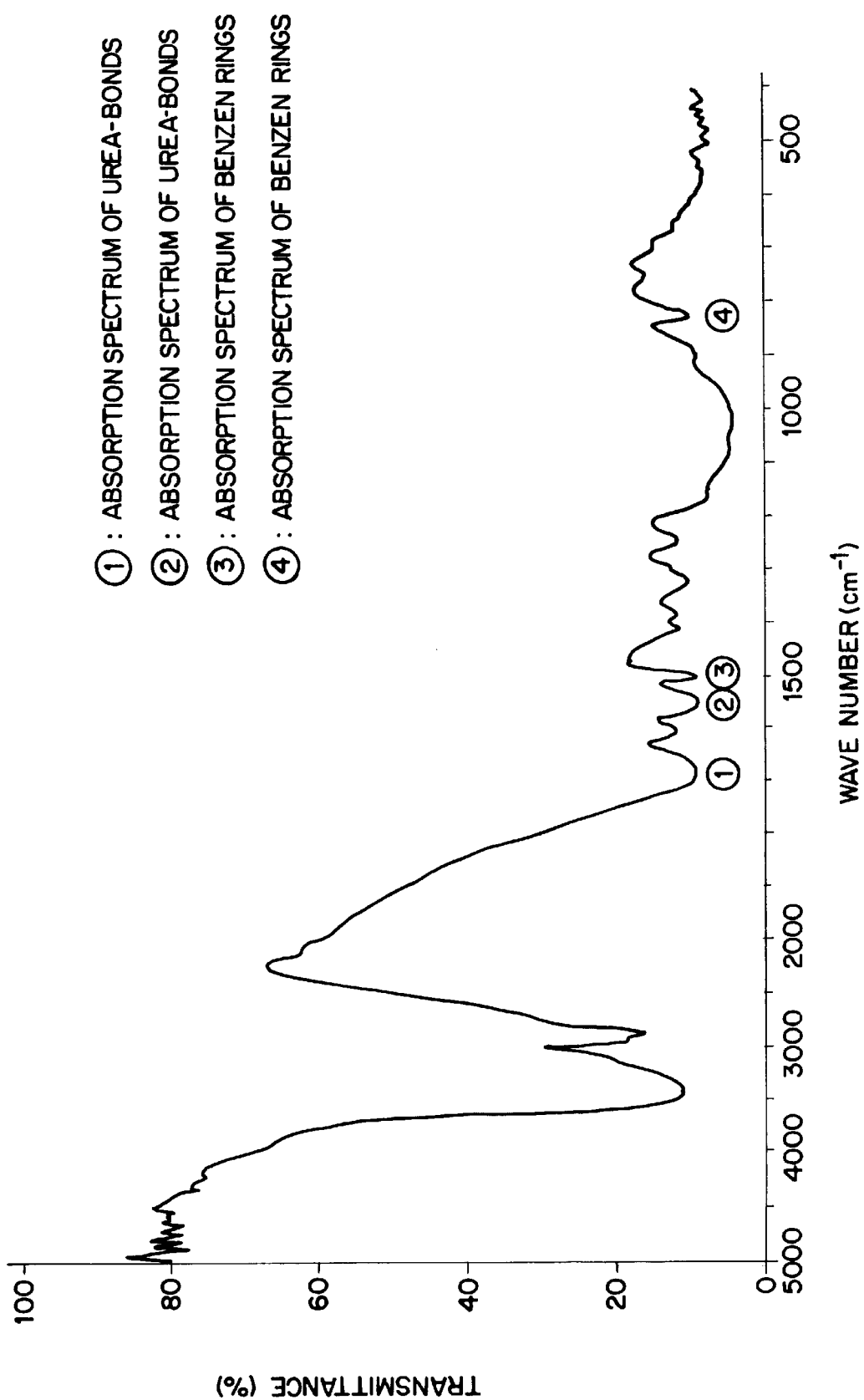
FIG. 1 shows an infrared spectrum of chitosan beads modified with p-chlorophenyl isocyanate.

This operation which needed 5 minutes per time was repeated 20 times to substitute N,N-dimethylformamide for the water content. These beads were gradually added into 100 ml N,N-dimethylformamide wherein 1 g p-chlorophenyl isocyanate was dissolved and the mixture was reacted for 1 hour at room temperature while it was stirred. Thereafter, the beads and the solution were separated using a glass filter and washing was performed by stirring these beads in 20 ml N,N-dimethylformamide for 5 minutes. This washing operation was repeated 20 times to eliminate completely unreacted p-chlorophenyl isocyanate. Then, a washing operation with distilled water was performed the same way to substitute distilled water for N,N-dimethylform-amide and chitosan beads with a structural formula (2) were obtained. Infrared spectrum of the modified chitosan beads is shown in FIG. 1.

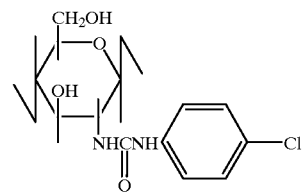
(2)

By using these modified chitosan beads (2) and unmodified chitosan beads (1) as a control, adsorption of four kinds of super antigens, namely, staphylococcal enterotoxin A (SEA), staphylococcal enterotoxin B (SEB), staphylococcal enterotoxin C (SEC) and toxic shock syndrome toxin-1 (TSST-1) were performed in a rabbit plasma. The initial concentrations of these super antigens were 1 ng/ml and 1 ml of the above described chitosan beads after being autoclaved under high pressure at 120° C. for 20 minutes was added into 10 ml plasma and the mixture was shaked at 37° C. for 60 minutes. The concentrations of four kinds of super antigens in the rabbit plasmas after reaction for 60 minutes were measured by means of an enzyme immune assay and the results were shown in Table 1. As shown by this result, super antigen adsorbability was provided to the chitosan beads by introducing urea bonds.

TABLE 1

Super antigen adsorption tests for four kinds of super antigens in rabbit plasmas using modified chitosan beads

|  | SEA pg/ml | SEB pg/ml | SEC pg/ml | TSST-1 pg/ml |
|---|---|---|---|---|
| Modified chitosan | 513 | 393 | 453 | 288 |
| Unmodified chitosan | 1163 | 1120 | 960 | 939 |

EXAMPLE 2

Figure 2:
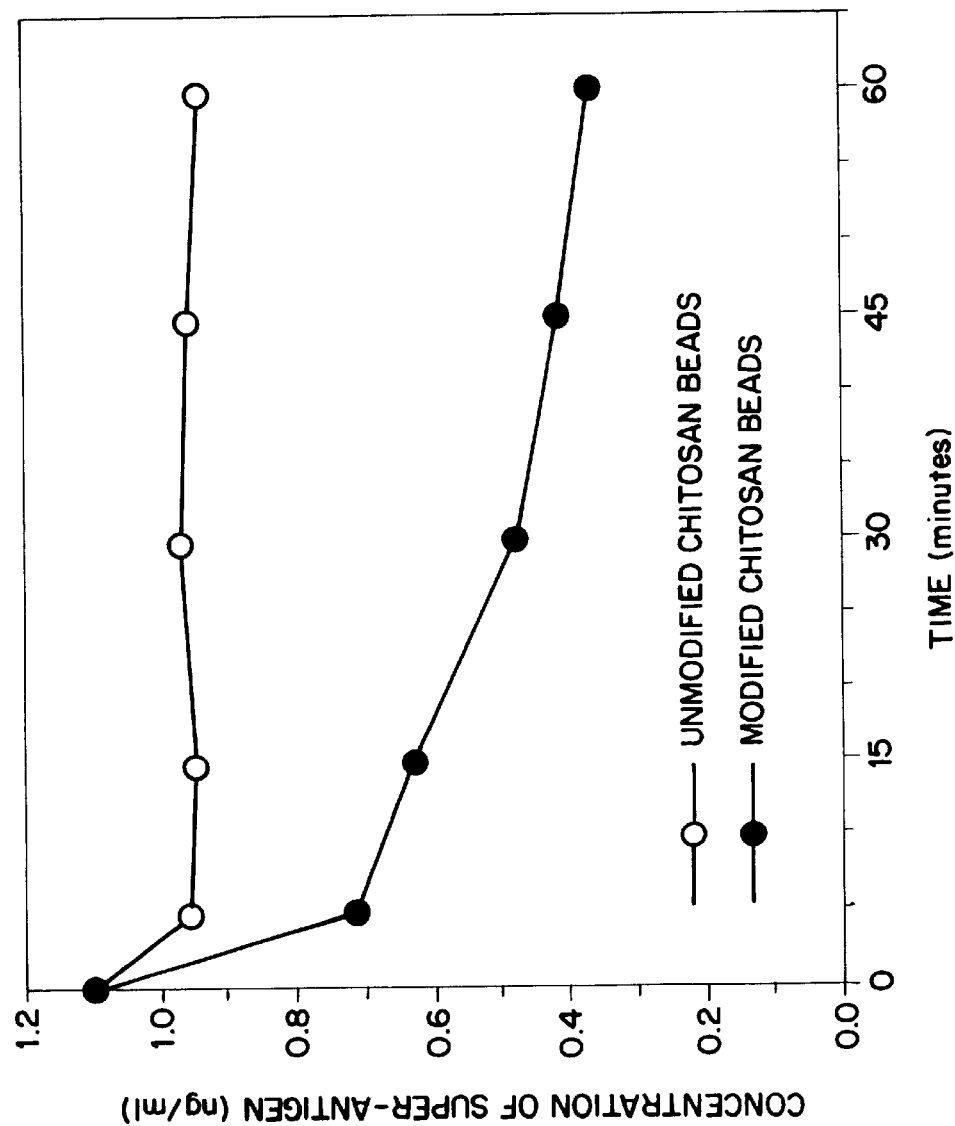
FIG. 2 shows the results of adsorption tests on super antigens by means of circulation method.

A super antigen adsorption test using modified chitosan beads-circulation method An adsorption test by means of a circulation method for a super antigen was performed using the unmodified chitosan beads (1) and the modified chitosan beads (2) of Example 1. 1 ml of the above described beads was filled in a column and 10 ml rabbit plasma wherein 1 ng/ml super antigen (TSST-1) was incorporated were circulated at 37° C. for 60 minutes. The concentrations in the rabbit plasma after 5, 15, 30, 45 and 60 minutes were measured by means of an enzyme immune assay and the results were shown in FIG. 2. Super antigen adsorbability under flow conditions similar to extracorporeal circulation were provided to the chitosan beads by introducing urea bonds like this.

EXAMPLE 3

Super antigen adsorption tests using seven kinds of chitosan beads wherein urea bonds or thiourea bond were introduced Phenyl isocyanate, p-tolyl isocyanate, 1-naphthyl isocyanate, phenyl isothiocyanate and p-chlorophenyl isothiocyanate were respectively reacted with chitosan beads by the same method as in Example 1. In addition, 4,4'-diphenylmethanediisocyanate and hexamethylenediisocyanate were reacted with chitosan beads by the same method as in Example 1 and then, terminal isocyanate groups were hydrolyzed by reacting them with distilled water for 12 hours at room temperature. Thereafter, the beads were washed thoroughly with distilled water: Modified chitosan beads each with structural formulae (3)–(9) were obtained by the above described method. Formulae (8) and (9) correspond "CHITOPEARL BCW-3501" and "CHITOPEARL BCW-3501", respectively.

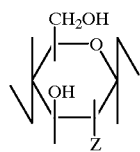

(3)

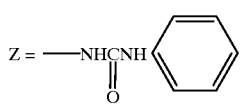

(4)

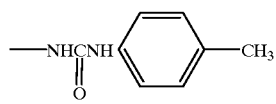

(5)

(6)

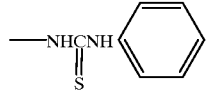

(7)

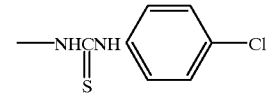

(8)

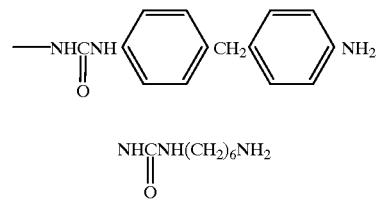

(9)

$$NH\overset{\text{O}}{\underset{\|}{C}}NH(CH_2)_6NH_2$$

By using these seven kinds of modified chitosan beads and unmodified chitosan beads as a control, adsorption of super antigen (TSST-1) was performed from rabbit plasma in the same way as in Example 1. The initial concentration of TSST-1 was 1 ng/ml and 1 ml of the above described chitosan beads was added into 10 ml plasma, and the mixture was shaked at 37° C. for 60 minutes and the concentrations of TSST-1 in the rabbit plasmas after reaction were measured by means of an enzyme immune assay. The concentrations of TSST-1 after 60 minutes are shown in Table 2.

TABLE 2

Adsorption tests of TSST-1 from rabbit plasmas using seven kinds of modified chitosan beads

| Structural formula | TSST-1 concentration (pg/ml) |
|---|---|
| 1 | 923 |
| 3 | 335 |
| 4 | 415 |
| 5 | 343 |
| 6 | 632 |
| 7 | 290 |
| 8 | 292 |
| 9 | 807 |

The structural formula (1) was for unmodified chitosan beads. As these results showed, super antigen adsorbability was provided to the chitosan beads by introducing urea bonds or

EXAMPLE 4 introduction of urea bonds into cellulose beads and a super antigen adsorption test using said beads 12 ml (it was sedimentary volume) aminated cellulose beads ("Amino-Cellulofine" manufactured by Chisso Co., Ltd., Tokyo Japan) with a structural formula (10) and a particle diameter of about 0.2 mm were stirred in 20 ml N,N-dimethylformamide for five minutes. Then the beads and the solution were separated by means of a glass filter.

(10)

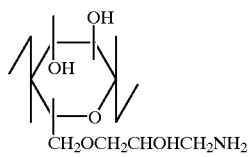
CH₂OCH₂CHOHCH₂NH₂

This operation was repeated 20 times to substitute completely N,N-dimethylformamide for water content.

These beads were gradually added into 100 ml N,N-dimethylformamide wherein 0.1 g 4,4'-diphenylmethanediisocyanate was dissolved and the mixture was reacted for 1 hour at room temperature while it was stirred. Thereafter, the beads and the solution were separated using a glass filter and washing was performed by stirring these beads in 20 ml N,N-dimethylformamide for 5 minutes. This washing operation was repeated 20 times to eliminate completely unreacted 4,4'-diphenylmethanediisocyanate. Then, it was reacted with the distilled water at room temperature for 12 hours and the terminal isocyanate groups were hydrolyzed to prepare amino groups. Thereafter, by washing thoroughly the beads with distilled water cellulose beads were obtained with a structural formula (11).

(11)

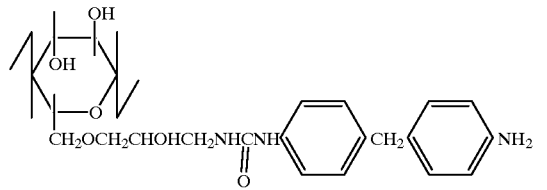

By using these modified cellulose beads (11) and unmodified cellulose beads (10) as a control, adsorption of a super antigen (TSST-1) were performed in rabbit plasma in the same way as in Example 1. The initial concentration of TSST-1 was 1 ng/ml and 1 ml of the above described cellulose beads was added into 10 ml plasma and the mixture was shaked at 37° C. for 60 minutes. The concentration of TSST-1 after the reaction was measured by an enzyme immune assay and the concentration of TSST-1 after 60 minutes are shown in Table 3.

TABLE 3

TSST-1 adsorption from rabbit plasmas using modified cellulose beads

| | Concentration of TSST-1 (pg/ml) |
|---|---|
| Modified cellulose | 485 |
| Unmodified cellulose | 946 |

As shown by this result, super antigen adsorbability was provided to the cellulose beads by introducing urea bonds.

EXAMPLE 5 (COMPARATIVE EXAMPLE 1)

Comparative tests on adsorption functions of TSST-1 between beads with amide bonds and urethane bonds and beads with urea bonds.

Chitosan beads with amide bonds (structural formula (12)) were prepared by reacting chitosan beads ("CHITOPEARL AL-1" with a structural formula (1)) with p-chlorobenzoyl chloride. This was a product wherein urea bonds of chitosan beads with the structural formula (2) prepared in Example 1 were replaced with amide bonds.

(12)

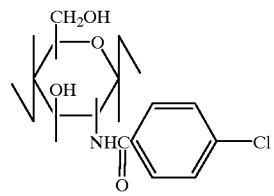

In addition, by the same method as that of Example 1, cellulose beads with urea bonds of structural formula (13) were prepared by reacting the aminated cellulose beads ("Amino-cellulofine" used in Example 4 with p-chlorophenyl isocyanate.

(13)

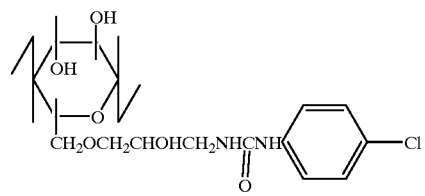

(14)

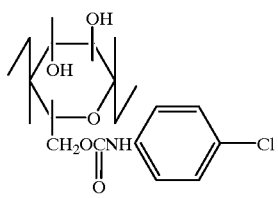

On the other hand, cellulose beads wherein urethane bonds were introduced (structural formula (14)) were prepared by reacting cellulose beads "Cellulofine GCL2000" with p-chlorophenyl isocyanate in the presence of triethylamine for 12 hours.

By using these beads, adsorption of super antigen (TSST-1) from rabbit plasma was performed. The initial concentration of TSST-1 was 1 ng/ml and 1 ml of the above described beads was added into 10 ml plasma and the mixture was shaked at 37° C. for 60 minutes. The concentrations of TSST-1 in the rabbit plasmas after reaction was measured by an enzyme immune assay and the results after 60 minutes are shown in Table 4.

TABLE 4

Comparative tests on adsorption functions of TSST-1 between beads with amide bonds or urethane bonds and beads with urea bonds (in rabbit plasma)

| Structural formula | Bonding mode | Concentration of TSST-1 (pg/ml) |
|---|---|---|
| (2) | Urea bond | 310 |
| (12) | Amide bond | 947 |
| (13) | Urea bond | 398 |
| (14) | Urethane bond | 972 |

As shown by this result, super antigen adsorbability was not provided by introducing amide bonds and urethane bonds and only in the case of urea bonds, super antigen adsorbability was provided.

EXAMPLE 6
Confirmation of super antigen specificity

By using modified chitosan beads (the structural formula (2)) prepared in Example 1, adsorbability to TSST-1 as a super antigen was investigated and adsorbabilities to bovine serum albumin (BSA) and human immunoglobulin G (IgG) as non-super antigens were investigated. Each protein was dissolved in rabbit plasma so as to obtain the concentration of 1 ng/ml. 1 ml of the above described beads was added into 10 ml of the plasma, the mixture was shaken at 37° C. for 60 minutes and the concentration of the protein in the plasma after reaction was measured by the enzyme immuno assay. The concentrations of the protein after 60 minutes are shown in Table 5. As these results showed, super antigen adsorbability was provided by introducing urea bonds but there was no adsorbability to other proteins while high specificity to super antigens was exhibited.

TABLE 5

Adsorption characteristics of various proteins using modified chitosan beads

|  | Concentration of protein |
| --- | --- |
| TSST-1 | 345 pg/ml |
| Bovine serum albumin | 946 pg/ml |
| Immunoglobulin G | 946 pg/ml |

EXAMPLE 7
Preparation of polyurea derivatives 0.32 g 1,3-diamino-2-hydroxypropane (hereinafter abbreviated as DAHP) was dissolved in 40 ml dimethyl sulfoxide (hereinafter abbreviated as DMSO). 10 ml DMSO solution wherein 0.63 g 4,4'-diphenylmethanediisocyanate (hereinafter abbreviated as MDI) was dissolved were dropped into this solution while it was stirred. After the whole amount of 10 ml was dropped, reaction was performed at 25° C. for one hour. Thereafter, 50 ml distilled water were added into the reaction liquid while it was stirred. White precipitate formed here was recovered by centrifugal separation and the recovered precipitate was washed five times with 50 ml methanol. Then, the precipitate was dried under vacuum to obtain 0.88 g polyurea derivative (hereunder abbreviated as DAHP polyurea). Infrared spectrum of the polyurea derivative is shown in FIG. 3. As shown in FIG. 3, the existence of hydroxyl group and urea bond were confirmed. Similarly, another polyurea derivative (hereunder abbreviated as DAP poyurea) was obtained using 1,3-diaminopropane (hereunder abbreviated as DAP) instead of DAHP.

EXAMPLE 8

Adsorption tests of super antigens using polyurea derivatives prepared in Example 7 were performed by the same method as that in Example 1. As a control, a polyurethane derivative prepared in the same way as Example 7 except that 1,3-propanediol was used instead of DAHP and that triethylamine was added in the reaction mixture and that the reaction was performed for 12 hours.

The initial concentrations of SEA, SEB, SEC and TSST-1 were 1 ng/ml and each 1 ml of DAHP polyurea, DAP polyurea, polyurethane was added in 10 ml plasma and the mixture was shaken at 37° C. for 60 minutes. All of DAHP polyurea, DAP polyurea and polyurethane were used after high pressure steam sterilization at 121° C. for 20 minutes. The concentrations of four kinds of super antigens in rabbit plasma after 60 minutes reaction were measured by enzyme immuno assay and the results are shown in Table 6. As these results showed, although polyurethane does not adsorb super antigens, it became clear that polyurea adsorbs super antigens and by introducing hydroxyl groups to the polyurea, the adsorbability was improved.

TABLE 6

Adsorption tests of four kinds of super antigens in rabbit plasma using polyurea

|  | SEA pg/ml | SEB pg/ml | SEC pg/ml | TSST-1 pg/ml |
| --- | --- | --- | --- | --- |
| DAHP polyurea | 320 | 357 | 333 | 435 |
| DAP polyurea | 728 | 810 | 735 | 749 |
| polyurethane | 925 | 880 | 956 | 890 |

EXAMPLE 9

Preparation of polystyrene fiber with a hydroxyl group-containing urea derivative on its side chain Islands-in-sea type composite fiber described in U.S. Pat. No. 4,661,260 (thickness: 2.6 denier; number of the islands:16) comprising of 50 wt parts of sea component (mixture of 46 wt parts of polystyrene and 4 wt parts of polypropylene) and 50 wt parts of islands component (polypropylene) were reacted in a mixed solution of 50 g of N-methylol-α-chloracetamide, 400 g of nitrobenzene, 400 g of 98% sulfuric acid and 0.85 g of paraformaldehyde at 20° C. for one hour. Then the fiber was washed with nitrobenzene, and thrown into water to stop the reaction. After that, the fiber was washed again with warm water. Thus, chloroacetoamidemethylated crosslinked polystyrene fiber (hereinafter abbreviated as AMPSt fiber) was obtained.

10 g DAHP were dissolved in 500 ml DMSO. 20 g AMPSt fiber (it corresponded to 20 mmol chloro content) were added into this solution while it was stirred. The reaction was performed at 25° C. for 6 hours. Thereafter, AMPSt fiber was washed on a glass filter with 500 ml DMSO and then, successively with 50 ml N,N-dimethylformamide. After washing, 1 g each of AMPSt fiber was added into 50 ml DMF wherein one of the below described isocyanates or isothiocyanates was dissolved.

TABLE 7

Isocyanates or isothiocyanates used for reaction with polystyrene fiber

| Reaction product | Isocyanates or isothiocyanates used for reaction |
| --- | --- |
| (a) | 0.23 g phenyl isocyanate |
| (b) | 0.30 g para-chlorophenyl isocyanate |
| (c) | 0.30 g meta-chlorophenyl isocyanate |
| (d) | 0.30 g ortho-chlorophenyl isocyanate |
| (e) | 0.27 g para-fluorophenyl isocyanate |
| (f) | 0.32 g para-methoxyphenyl isocyanate |
| (g) | 0.26 g para-tolyl isocyanate |
| (h) | 0.32 g para-nitrophenyl isocyanate |
| (i) | 0.33 g 1-naphthyl isocyanate |
| (j) | 0.48 g 4,4'-diphenylmethanediisocyanate |
| (k) | 0.70 g 3,3',5,5'-tetraethyl-4,4'-diisocyanate-diphenylmethane |
| (l) | 0.24 g cyclohexyl isocyanate |

TABLE 7-continued

Isocyanates or isothiocyanates used for reaction with polystyrene fiber

| Reaction product | Isocyanates or isothiocyanates used for reaction |
|---|---|
| (m) | 0.33 g hexamethylenediisocyanate |
| (n) | 0.19 g n-butyl isocyanate |
| (o) | 0.26 g phenyl isothiocyanate |
| (p) | 0.33 g para-chlorophenyl isothiocyanate |
| (q) | 0.27 g cyclohexyl isothiocyanate |
| (r) | 0.22 g n-butyl isothiocyanate |

The reaction was performed at 25° C. for one hour. Thereafter, the reaction product was washed on a glass filter with 200 ml DMSO and 500 ml distilled water. The compounds obtained from the reaction with each isocyanate or isothiocyanate were named as (a)–(r).

In addition, a part of AMPSt fiber wherein p-nitrophenyl group was introduced by reacting p-nitrophenyl isocyanate was added into 100 ml sodium hydrosulfite water solution (0.1 g/ml) and it was converted into p-aminophenyl group by reduction at 60° C. for 4 hours (it was made as the compound (s).).

EXAMPLE 10

Adsorption of super antigens using polystyrene fibers with urea derivatives on their side chains Adsorption tests of super antigens using modified polystyrene fibers prepared in Example 9 were performed by the same method as that in Example 1. The initial concentrations of SEA, SEB, SEC and TSST-1 were 1 ng/ml and each 1 g of the modified ANIPSt fiber was added in 10 ml plasma and the mixture was shaken at 37° C. for 60 minutes. The modified AMPSt fibers were used after high pressure steam sterilization at 120° C. for 20 minutes. The concentrations of four kinds of super antigens in rabbit plasma after 60 minutes reaction were measured by enzyme immuno assay and the results are shown in Table 8.

As a control, an AMPSt fiber (t) wherein amide bonds were introduced instead of urea bonds by reacting benzoyl chloride instead of isocyanate under the same condition was used. In addition to that, an AMPSt fiber (u) wherein phenyl isocyanate was reacted after DAP was reacted instead of DAHP was also evaluated.

As these results showed, it became clear that as the polystyrene fiber (t) where there was no urea bond exhibited no adsorbability of super antigens; adsorbability of super antigens was exhibited by introducing urea bonds. In addition, it was shown that higher adsorbability of super antigens was exhibited by modifying with an aromatic isocyanate than with an aliphatic isocyanate. In addition, the adsorbability of super antigens was reinforced by introducing hydroxyl groups.

TABLE 8

Adsorption of super antigens using polystyrene fibers each with a urea derivative on their side chains

| Modified AMPSt | SEA pg/ml | SEB pg/ml | SEC pg/ml | TSST-1 pg/ml |
|---|---|---|---|---|
| (a) | 450 | 382 | 360 | 462 |
| (b) | 330 | 382 | 365 | 399 |
| (c) | 332 | 381 | 362 | 352 |
| (d) | 450 | 462 | 475 | 488 |
| (e) | 400 | 412 | 386 | 428 |
| (f) | 723 | 733 | 584 | 669 |
| (g) | 448 | 285 | 363 | 433 |
| (h) | 621 | 588 | 589 | 603 |
| (i) | 425 | 335 | 385 | 418 |
| (j) | 352 | 350 | 330 | 320 |
| (k) | 768 | 812 | 750 | 796 |
| (l) | 766 | 801 | 789 | 732 |
| (m) | 682 | 762 | 787 | 698 |
| (n) | 702 | 785 | 788 | 776 |
| (o) | 463 | 355 | 354 | 477 |
| (p) | 336 | 375 | 358 | 401 |
| (q) | 770 | 798 | 774 | 762 |
| (r) | 777 | 774 | 793 | 802 |
| (s) | 822 | 852 | 885 | 856 |
| (t) | 975 | 985 | 1022 | 1005 |
| (u) | 802 | 798 | 822 | 785 |

EXAMPLE 11

Preparation of polystyrene fiber with an amino group-containing urea derivative on its side chain 0.8 g triethylenetetramine was dissolved in 500 ml DMSO. 1.0 g AMPSt fiber (which corresponded to 2 mmol chloro content) were added into this solution while it was stirred. The reaction was performed at 25° C. for 12 hours. Thereafter, AMPSt fiber was washed on a glass filter with 500 ml DMSO and then, successively with 50 ml N,N-dimethylformamide. After washing, the AMPSt fiber was added into 50 ml DMF in which 0.30 g p-chlorophenyl isocyanate had been dissolved. Thereafter, AMPSt fiber was washed on a glass filter with 200 ml DMSO and then, successively with 200 ml distilled water and AMPSt fiber (v) was obtained.

EXAMPLE 12

Adsorption of super antigens using polystyrene fibers with an amino group-containing urea derivatives on their side chains By using the AMPSt fiber (v) obtained by Example 11, adsorption of super antigens were performed in the same way as Example 1. As a control, AMPSt fiber (t) used in Example 10 was used. The initial concentrations of SEA, SEB, SEC and TSST-1 were 1 ng/ml and 1 g of the above described AMPSt (v) fiber were incorporated into 10 ml plasma and the mixture was shaken at 37° C. for 60 minutes. Each AMPSt (v) fiber was used after being sterilized under high pressure steam at 121° C. for 20 minutes. The concentrations of four kinds of super antigens in the rabbit plasmas after reaction for 60 minutes were measured by an enzyme immune assay and the results are shown in Table 9. As shown by this result, it is clear that an amino group-containing urea derivative has super antigen adsorbability.

TABLE 9

Adsorption of super antigens using polystyrene fibers with an amino group-containing urea derivative on their side chains

| Modified AMPSt | SEA pg/ml | SEB pg/ml | SEC pg/ml | TSST-1 pg/ml |
|---|---|---|---|---|
| (V) | 241 | 287 | 302 | 197 |
| (T) | 956 | 1001 | 981 | 975 |

EFFECT OF THE INVENTION

A material containing urea bonds or thiourea bonds with excellent selective binding characteristics with super antigens even in a high protein concentration solution in the neutral region and remaining activity even after sterilization and being inexpensive was provided by the present invention. By using the material of the present invention, it is possible that the activities of super antigens existing in body fluids such as blood and urine, foods, drinks and medicines can be removed (detoxified), it is possible to treat food poisoning, sepsis and autoimmune diseases and to prevent them from occurring. In addition, as it is possible using water-insoluble materials to eliminate efficiently super antigens from body fluids such as blood and urine, foods, drinks and medicines, by a super antigen eliminating column and a wound dressing material, it is possible to treat food poisoning, sepsis and autoimmune diseases and to prevent them from occurring. In addition, as the material of the present invention can be used as a measuring material, it is possible to diagnose food poisoning, sepsis and autoimmune diseases.

What is claimed is:

1. A method of detoxifying or removing a super antigen from a fluid containing same, said method comprising passing the super antigen-containing fluid through a column filled with a material composed of a compound of formula (I)

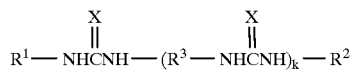

wherein said method comprises a group capable of forming a hydrogen bond and an aromatic substituent and,
X is O or S;
k is 0 or a positive integer;
each of $R^1$, $R^2$, $R^3$ is a group capable of forming a hydrogen bond or an aromatic substituent.

2. A method according to claim 1, wherein a unit having a group capable of forming a hydrogen bond and a unit having an aromatic substituent are alternatively repeated.

3. A method according to claim 1, wherein the group capable of forming a hydrogen bond is an amino group.

4. A method according to claim 3, wherein the amino group is secondary or tertiary amino group.

5. A method according to claim 1, wherein the group capable of forming a hydrogen bond is a hydroxyl group.

6. A method according to claim 5, a wherein the hydroxyl group is a hydroxyl group of a glucide or its derivative.

7. A method according to claim 1, wherein the aromatic substituent is a phenyl group, a naphthyl group or their derivative at least one of which hydrogen is substituted with F, Cl, Br, $CH_3$, $C_2H_5$, $NO_2$, $OCH_3$ or $CH_2PhNH_2$.

8. A method according to claim 1 wherein $R^1$ and/or $R^3$ containing a structure of formula (II)

where n and m are selected from an integer of 0–10.

9. A method according to claim 1 wherein $R^1$ and/or $R^3$ containing a structure of formula (III)

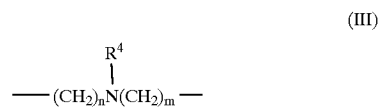

where $R^4$ is hydrogen or alkyl group having 1–10 carbon atoms, n and m are selected from the integers of 0–10.

10. A method according to claim 1, wherein the k is the positive integers of 1 to 200.

11. A method of detoxifying or removing a super antigen from a fluid by passing the super antigen-containing fluid through a column filled with a material for elimination or detoxification which comprises urea bond or thiourea bond.

12. A method of detoxifying or removing a super antigen according to claim 11, wherein the fluid is a blood, plasma or serum.

13. A method of detoxifying or removing a super antigen from blood or plasma, comprising the successive steps of:
   (a) removing blood or plasma from a mammal under conditions which prevent coagulation;
   (b) contacting the blood or plasma with a material for elimination or detoxification which comprises urea bond or thiourea bond;
   (c) separating the blood or plasma from the material; and
   (d) returning the blood or plasma to the mammal.

14. A method according to claim 11 wherein said material comprises an aromatic ring.

15. A method according to claim 11, wherein said material comprises a group which is capable of forming hydrogen bond.

16. A method according to claim 11, wherein said group which is capable of forming hydrogen bond is an amino group.

17. A method according to claim 16, wherein said amino group is a secondary or tertiary amino group.

18. A method according to claim 15 wherein said group which is capable of forming a hydrogen bond is a hydroxyl group.

19. A method according to claim 18 wherein said hydroxyl group is a hydroxyl group of a glucide.

20. A method according to claim 19 wherein said glucide is at least one selected from the group consisting of chitosan, cellulose or a derivative thereof.

21. A method according to claim 11 wherein said material comprises a substrate.

22. A method according to claim 21 wherein said substrate comprises a member selected from the group consisting of polystyrene, polysulfone, polymethyl methacrylate and their derivatives.

23. A method according to claim 22 wherein said substrate is a fiber.

24. A method according to claim 23 wherein said fiber is an islands-in-sea fiber.

25. A method according to claim 11 wherein said material is water-insoluble.

* * * * *